United States Patent [19]
Chalifoux

[11] Patent Number: 5,362,237
[45] Date of Patent: * Nov. 8, 1994

[54] DENTAL POST CONSTRUCTION

[75] Inventor: Paul R. Chalifoux, Wellesley, Mass.

[73] Assignee: Wellesley Research Associates, Inc., Wellesley, Mass.

[*] Notice: The portion of the term of this patent subsequent to Jan. 11, 2011 has been disclaimed.

[21] Appl. No.: 75,329

[22] Filed: Jun. 11, 1993

Related U.S. Application Data

[63] Continuation-in-part of Ser. No. 908,366, Jul. 6, 1992, which is a continuation-in-part of Ser. No. 896,388, Jun. 10, 1992, which is a continuation-in-part of Ser. No. 739,670, Aug. 2, 1991, Pat. No. 5,277,583.

[51] Int. Cl.$^5$ .............................................. A61C 5/08
[52] U.S. Cl. ..................................... 433/220; 433/221
[58] Field of Search ................. 433/220, 221, 76, 165, 433/166

[56] References Cited

U.S. PATENT DOCUMENTS

| | | | |
|---|---|---|---|
| 635,773 | 10/1899 | Hamilton | 433/220 |
| 636,568 | 11/1899 | Seeley | 433/221 |
| 781,420 | 1/1905 | Haldeman | 433/220 |
| 791,641 | 6/1905 | McClanahan | 433/220 |
| 1,200,921 | 10/1916 | Chester | 423/165 |
| 2,807,264 | 9/1957 | Tuck | 433/166 |
| 3,508,334 | 4/1970 | Weissman | 433/76 |
| 4,820,159 | 4/1989 | Weissman | 433/165 |
| 4,990,088 | 2/1991 | Weissman | 433/165 |
| 5,094,618 | 3/1992 | Sullivan | 433/221 |

Primary Examiner—Cary E. O'Connor
Attorney, Agent, or Firm—Paul J. Cook

[57] ABSTRACT

A dental post is provided comprising a top section and a stem with a slot which extends lengthwise through the stem to form a plurality of legs. The legs have wings attached thereto which fit into indentations in a wall of a tooth bore. Kits are provided comprising the dental post and burs for forming a tooth bore to accommodate the dental post and optionally a core for supporting a tooth crown, a template for forming holes in a tooth stub and a key for providing support for the core.

23 Claims, 4 Drawing Sheets

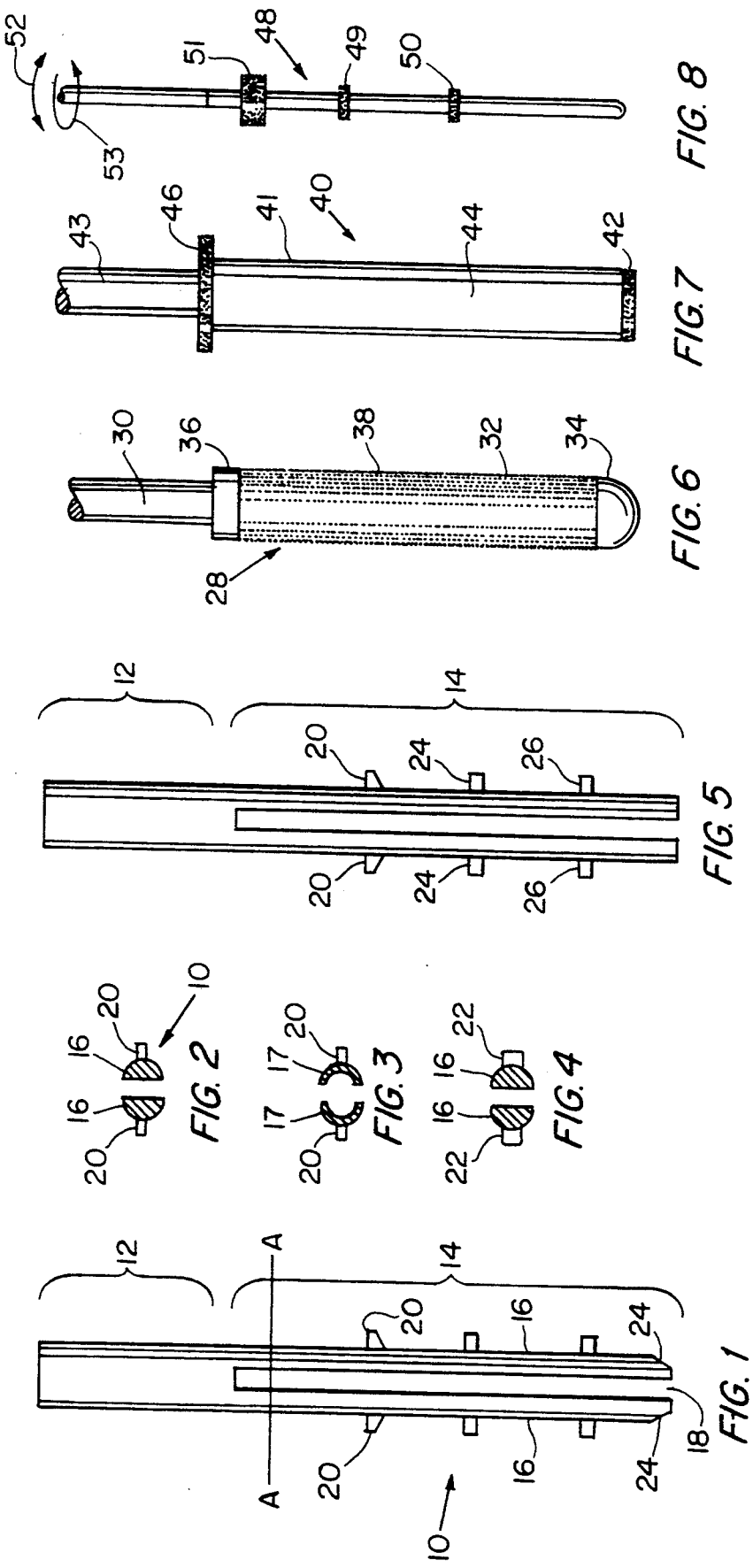

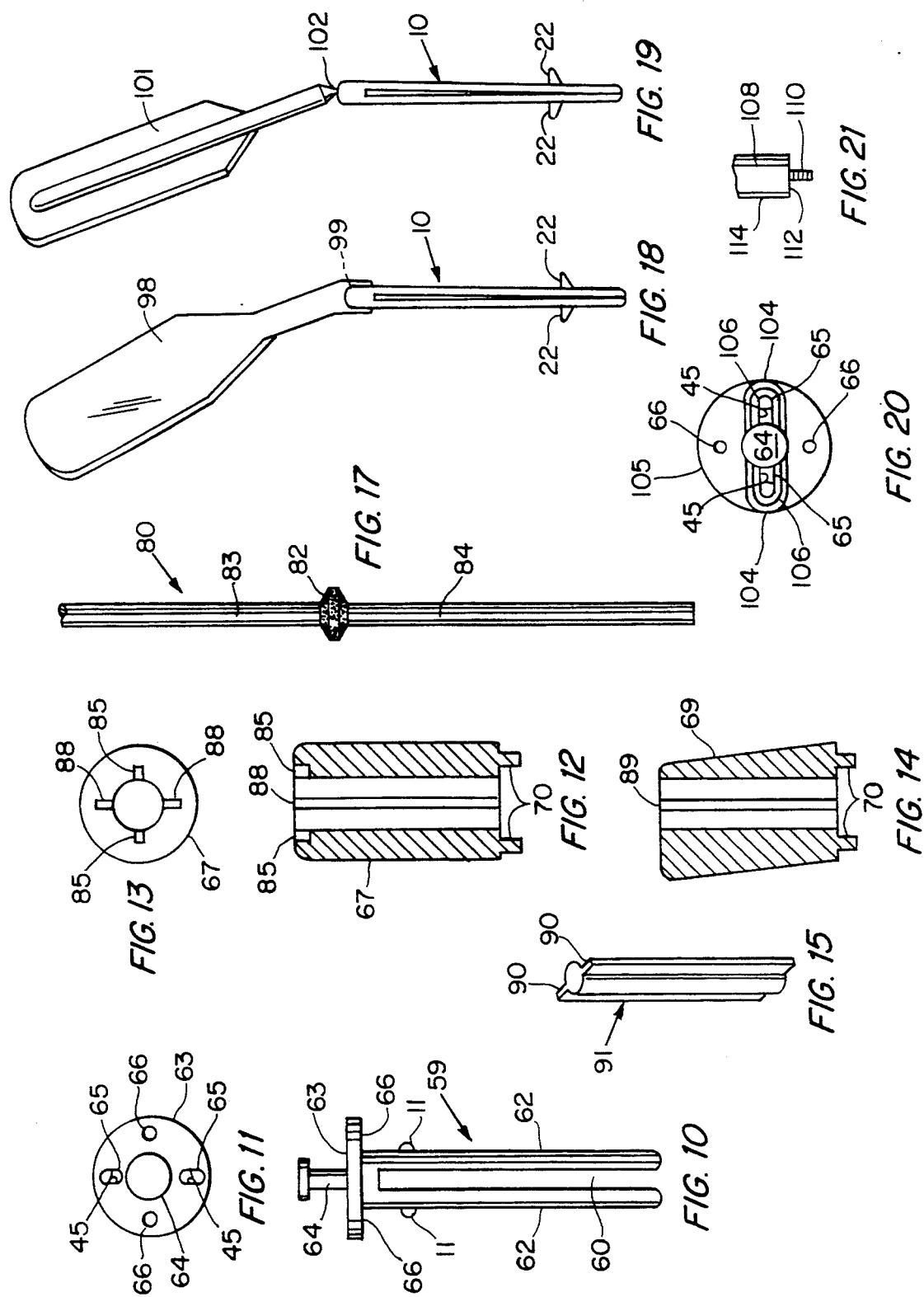

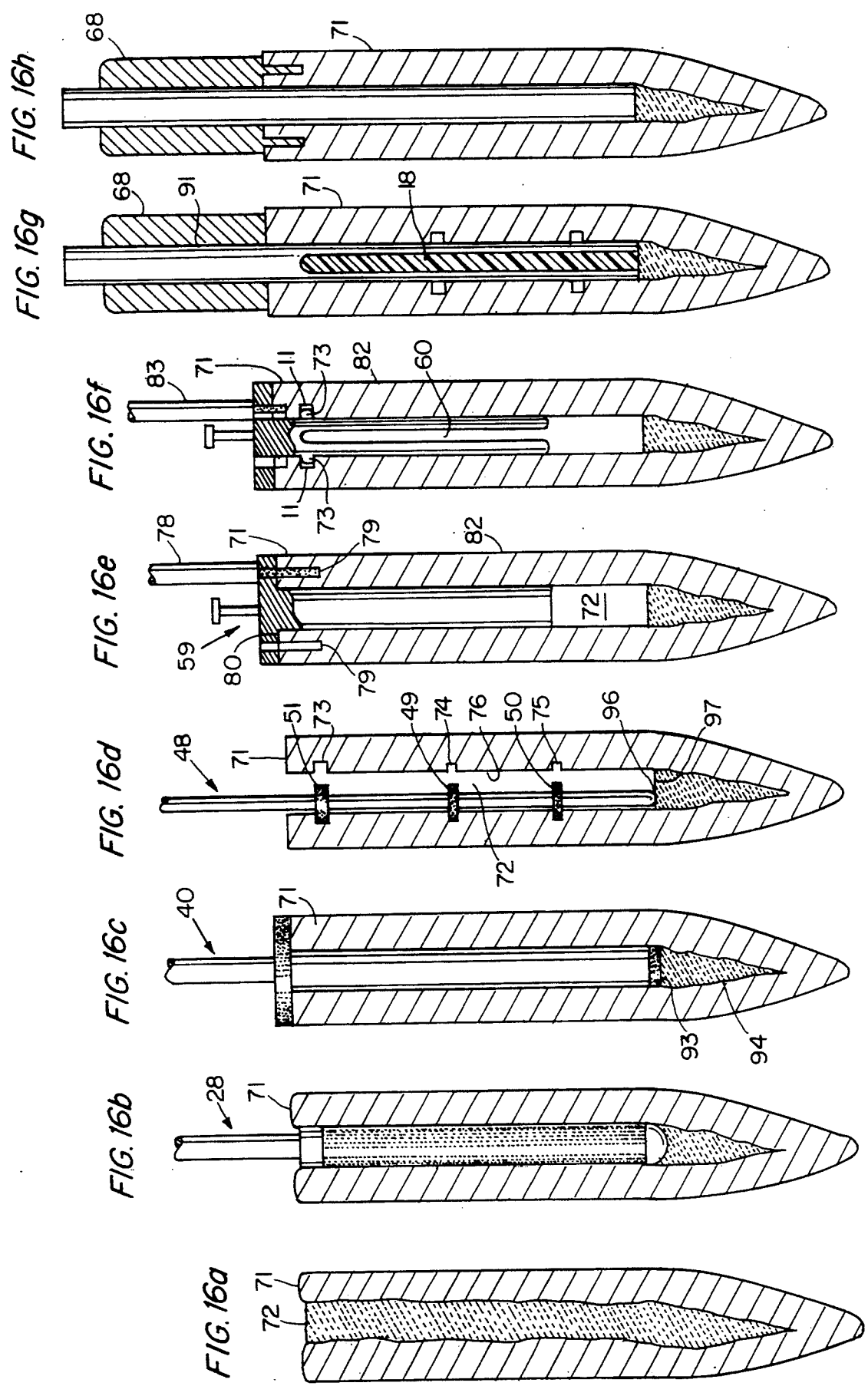

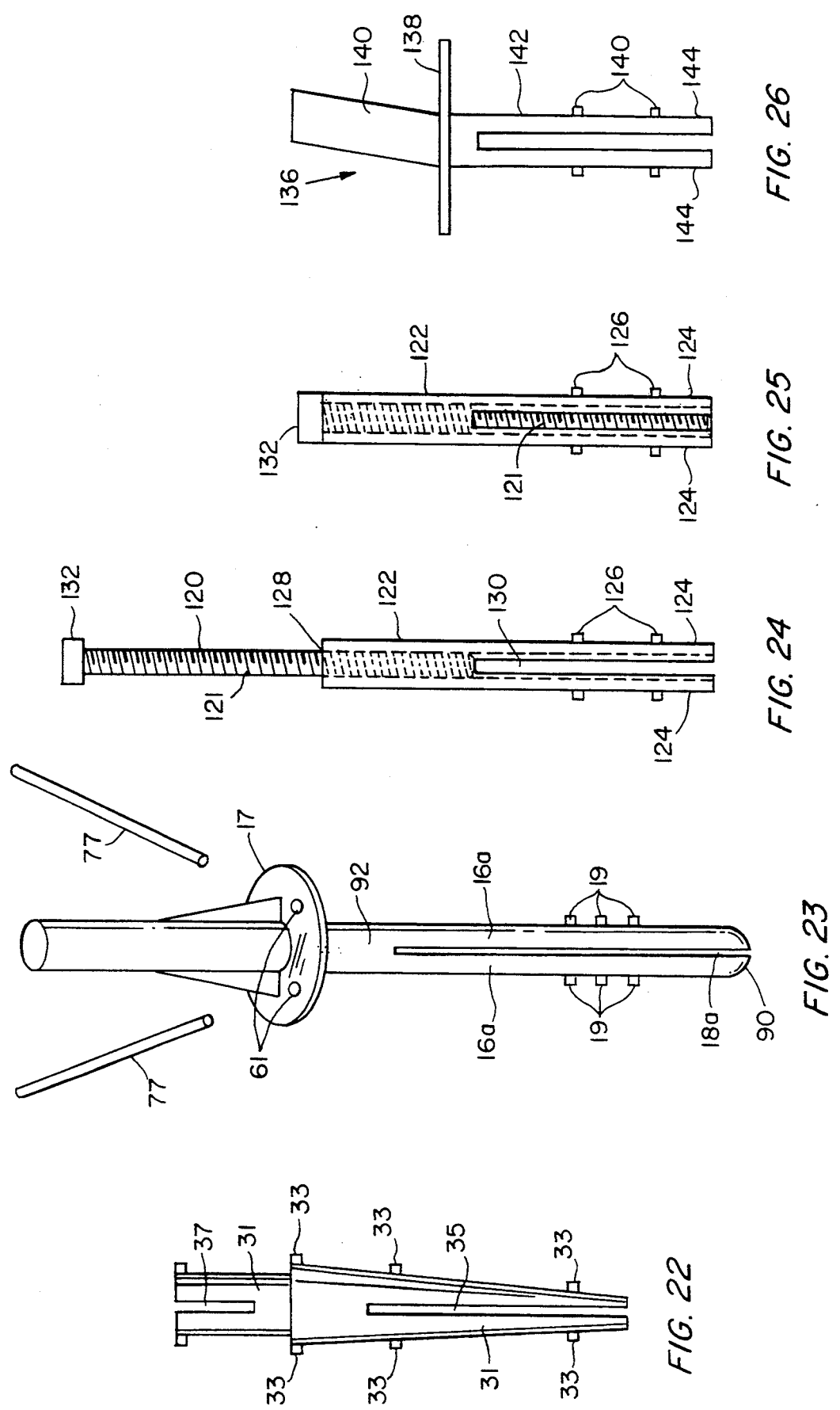

DENTAL POST CONSTRUCTION

REFERENCE TO RELATED APPLICATIONS

This application is a continuation in part of Ser. No. 07/908,366, filed Jul. 6, 1992, pending, which, in turn, continuation in part of Ser. No. 07/896,388, filed Jun. 10, 1992, pending, which, in turn, is a continuation in part of application Ser. No. 07/739,670 filed Aug. 3, 1991, now U.S. Pat. No. 5,277,583.

BACKGROUND OF THE INVENTION

This invention relates to a dental post construction which can be inserted into a tooth stub and which is utilized to improve retention of a dental restoration built onto the tooth stub.

It is present dental procedure to form a dental prosthetic structure onto a tooth stub for replacement of missing dentition. In this procedure, a tooth stub is initially prepared by removing the diseased or damaged top portion of a tooth to form a tooth stub. A base is formed by drilling into the root canal portion of the tooth stub to form a space into which a dental post can be inserted. Presently available dental post include grooves on their surface designed to improve retention of the post within the tooth stub. Dental cement is employed in the bore in conjunction with the dental post to secure the post in the tooth stub. A portion of the post extends above the tooth stub upper surface so that a dental prosthesis formed on the tooth stub can be retained. Presently, the implantation of a dental post relies either upon the adherent strength of an adhesive or on lateral stress forces between the dental post and the canal wall of screw type posts.

Preformed posts are posts which are premade to specific dimensions with matching burs having cutting surfaces. The burs have a matching diameter to the past and prepare the root to accept a post. A post is then tried in the root and cut to the appropriate length. Cement is spun into the canal with a device referred to as a lenticulo spiral, placed directly with a syringe and/or placed directly on the post. The post is placed in the canal and held in position until excess cement extrudes and the cement hardens. Most preformed posts require placing filling material around the top of the post to transfer strength from the post to the crown. This procedure is referred to as the core build up or post and core procedure.

There are many problems which are encountered when utilizing preformed posts. These include:

An inaccurate fit develops with present bur technology.

Potential for perforation of the root is great with present burs.

There is inadequate resistance to rotational forces on the post.

Root fracture caused by lateral stresses occurs.

There is weak transfer of strength from the post to the crown positioned on the post.

An accurately drilled hole results in good proximity of the post to the canal walls with a thin cement layer to provide greater success in properly positioning the post. The hole is inaccurate if tipping or vibrating of the bur occurs during root preparation as occurs with present drilling systems. This adds to the failure rate of preformed post systems. Drilling a straight hole for a straight post in a curved canal or drilling a hole which does not align with a canal can lead to perforation of a root and loss of a tooth. All posts must resist normal rotational forces which occur during normal or abnormal functions if there is not sufficient tooth structure to provide resistance. In general, preformed posts do not provide good stability against rotational force because they are round and rotate easily when placed in a round hole such as that provided by present bur systems. Presently, to compensate for this, a separate pin may be placed into the tooth, however, screw pins increase the likelihood of root fracture. Some systems try to make posts oval or non-symmetrical at the top but do not supply dependable resistance and retention form. Cement merely provides suction to hold a post in position. The strength of the cement becomes a weak point to the root-post-crown relationship. Constant repeated forces of chewing causes potential breakdown on the tooth-cement-crown interface with subsequent cement wash out and crown post failure. An uneven or excessive amount force can cause root fracture and tooth loss. Screw type posts can exert large lateral stresses which leads to potential root fracture and tooth loss. In addition, forceful placement of cement type posts without proper venting of cement can cause root fracture and tooth loss. Filling material is placed around a preformed post above the root to accept a crown after the post is cemented. The strength and long term stability of this material becomes a weak link in long term success of the crown. In addition, proper design of the post above the root is critical to resist rotation or dislodging of the filling material from the post.

A cast post is inducted for root canalled teeth with no clinical crown (no tooth above the height of the gums) and/or teeth with root canal spaces which are shaped in such a manner that a preformed post can not fit properly. For example, a canal may be narrow at its bottom half and diverge rapidly in the top half or it may be too oval shaped. The preformed post which is of the same diameter throughout can not accommodate these situations. When utilizing a cast post, root preparation is done by drilling to remove undercuts and obtain slight divergence from the bottom upward. The cast post technique takes an impression of a prepared root canal space. In indirect methods, an impression of the root is taken with a dental impression material. In direct methods, an acrylic pattern of the prepared root and the desired shape above the gums is achieved in the mouth. Laboratory procedures which include casting in a lost wax technique are then necessary to construct the cast post. There are many problems which are encountered when utilizing casts posts. The problems include: An increased chance of root fracture. The cast post is expensive. There is an increased possibility of root perforation. The cast post may not provide good resistance to rotational forces.

All posts need to provide venting of cement as a post is placed. A cast post is very precise fitting so it is difficult for cement to vent, lateral forces can fracture the root and/or the post will not be fully seated as excess cement remains in the bottom. In addition, any bubbles or inaccuracies from the casting process can cause a poor fit and root fracture. Cast posts dramatically increases cost as compared to preformed posts because there are laboratory fees and increased time required to treat the patient. For a cast post, an appointment is needed for an impression in addition to an appointment for post placement. The patient cost of a cast post is double the cost of a preformed post. The doctor's laboratory cost may be five to ten times the cost to buy a preformed post.

Preparation of a root canal space must be free of any undercuts or removal of a cast post in its plastic or wax phase of construction will be impossible. It is often difficult to attain this as root canals tend to be complex systems of lateral canals, ribbon shapes, multiple canals, etc. Often, excessive drilling is done which removes important tooth structure and leads to a weaker root and increased chance of root fracture or perforation.

It has been proposed in U.S. Pat. Nos. 4,480,997; 4,490,116 and Re 31,948 to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. In addition, the possibility exists that the post will be threaded too far into the tooth stub which will result in fracture of the tooth stub. Furthermore, the radially outward forces of the legs on the tooth stub can result in fracture of the tooth stub over time.

U.S. Pat. No. 1,534,409 discloses a two legged post having corrugated surfaces which fit into a root canal having generally parallel walls. This surface design materially reduces the post surface area which contacts the canal walls and thus post retention relies primarily upon cement adhesive strength.

U.S. Pat. No. 791,641 discloses a crown construction adapted to be fit in the surface of a tooth stump. A pin is provided having a lower one sided end adapted to fit into a root canal and a split upper portion having legs which are forced apart from each other by means of a wedge. In the absence of the wedge, the legs contact each other by spring forces which must be overcome by the force exerted by the wedge. The legs have lugs which fit into recesses of the crown after the wedge is inserted. No lugs are provided on the portion of the pin which is inserted into the root canal. This structure is understandable due to the force required to position it into a root canal. These required forces undesirably enhance the possibility of fracturing the tooth structure after the pin is positioned.

Accordingly, it would be desirable to provide a dental post which can be inserted into the bore of a tooth stub while eliminating the need for sole reliance upon lateral stress forces with the canal wall or upon the adhesive strength of an adhesive. In addition, it would be desirable to provide a dental post which interacts with indentations in the walls of the bore by mechanical interaction in order to retain the post in the bore by mechanical interaction in order to retain the post in the bore while minimizing or eliminating forces on the walls exerted by the post. In addition, it would be desirable to provide a system for forming a mating hole in a tooth stub for such a dental post and for properly positioning the post manually within the bore. Furthermore, it would be desirable to provide a system for utilizing such a dental post which facilitates the placement of a core and a crown.

SUMMARY OF THE INVENTION

This invention provides a dental post having a stem section formed of a plurality of spaced-apart legs, usually two or four legs, which are joined to a top section. The top section is of a length so as to extend beyond an upper surface of the tooth stub thereby allowing retention of a prosthesis. The legs are spaced apart so as to allow manual compression. At least two legs are provided with at least one wing section extending radially outward from the surface of the leg. Sets of wings are provided, on different legs which are positioned at the same vertical height from the bottom section of the post. A dental adhesive is placed in the bore prior to placing the post within the bore. The post is grasped either manually or mechanically to compress the legs together so that the wings are positioned radially inwardly from the wails of the bore. In this position, the post can be moved within the bore, vertically, horizontally or rotationally until the wings are positioned into mating slots previously formed within the walls of the bore. The compression force on the legs is released when the wings have entered the bore. Upon the wings entering the mating slots, lateral force of the legs is released. The noncompressed legs exert little or no expansion force on the bores wails being properly positioned. Suitable drill burs are provided to shape and position the slots in the bore walls to mate properly with the wings on the legs of the dental post.

BRIEF DESCRIPTION OF THE DRAWINGS

FIG. 1 is a side view of a dental post of this invention.

FIGS. 2, 3 and 4 show alternative cross sections of the legs of the post of FIG. 1 taken along line A—A.

FIGS. 6, 7 and 8 are side views to illustrate a set of drill burs which can be utilized in conjunction with the dental post of this invention.

FIG. 9 is a side view of a drill bur which can be utilized to replace the drill bur of FIG. 8.

FIG. 10 is a side view of a template which can be utilized in conjunction with this invention.

FIG. 11 is a top view of the template of FIG. 10.

FIG. 12 is a cross section view of a core which can be utilized in conjunction with the dental post of this invention.

FIG. 13 is a top view of the core of FIG. 12.

FIG. 14 is a cross sectional view of an alternative core which can be utilized in conjunction with the dental post of this invention.

FIG. 15 is an isometric view of a key device which can be utilized in conjunction with the dental post of this invention.

FIGS. 16a–h are cross sectional views illustrating the installation of the dental post of this invention.

FIG. 17 is a side view of a drill bur which can be utilized to replace the drill bur of FIG. 8.

FIG. 18 is a side view of a handle useful with the post of this invention.

FIG. 19 is a side view of an alternative handle useful with the post of this invention.

FIG. 20 is a top view of an alternative template useful in the system of this invention.

FIG. 21 is a side view of a bur useful with the template of FIG. 20.

FIG. 22 shows a tapered post of this invention.

FIG. 23 is an isometric view of an alternative post of this invention.

FIG. 24 is an isometric view of an alternative post of this invention.

FIG. 25 is an isometric view of the post of FIG. 24.

FIG. 26 is an isometric view of an alternative post of this invention.

DESCRIPTION OF SPECIFIC EMBODIMENTS

The dental post of this invention includes a means for locking it into the walls of a tooth bore without the requirement of maintaining the post under pressure, self induced or otherwise, against the bore walls. The dental post includes a stem having a slot which forms a plurality of legs. At least one leg includes a wing extending radially outward from the leg. The wing is shaped to mate with an indentation of the tooth bore wall which is formed with a drill bur. Each leg can include one or a plurality of wings, each of which mates with separate indentations in the wall. The legs are sufficiently flexible so that they can be compressed manually or mechanically for ease of insertion into and removal from the tooth bore. The surface of the legs can be roughened by any conventional technique such as by sand blasting, acid etching, molding or the like. The roughened surface provides an increased surface area which results in improved retention of the post within the canal. When the legs are compressed, so that the wings can fit within the opening of the tooth bore, the post is inserted into the bore. Once the wings have entered the bore of the tooth stub, compression force is released and the post is pressed in a downward direction until the wings engage matching slots resulting in the legs resuming a position essentially parallel to each other. The wings can be at the same or different heights. The wings can be the same or different sizes. It is advantageous to have wings with matching indentations which are greater size in height (from top of the wing to the bottom) at lower levels to allow an accurate fit in only one position. The legs are not prestressed so as to avoid exertion of a force by the legs on the bore walls. By eliminating this stress in the legs, the tooth stub is not subjected to a continuing expansion force from within the tooth stub. Therefore, the tooth stub is less likely to fracture during normal use as compared to a tooth stub containing a dental post that exerts a continuing expansion force. The indentations are formed by a set of drill burs which fit on conventional dental drills. The surface of the burs are designed to prepare the tooth bore for insertion of the dental post and to form the wall indentation which mate with the wing portions of the dental post.

In cases where the success of the root canal is questionable, the post can be implanted without employing a dental cement in the root canal. The wings mechanically lock into the wall indentations upon placement but disengage if the post is rotated ninety degrees. The elimination of cement within the canal is advantageous since, with present technology, when a root canal fails and a post is present, the post cannot be removed for retreatment of the root canal. This necessitates that surgery be done to the root to eliminate infection. When the post is removable, as in the case when cement within the canal is not utilized, surgery can be avoided and the root canal can be retreated to eliminate infection.

In one aspect of this invention, a system, including a template, burs and a core for a tooth crown, is provided for use in conjunction with the dental post of this invention. A template apparatus is inserted into the tooth bore. The template includes holes positioned and shaped to accommodate burs used to form holes on the tooth stub top surface in a shape and design to accommodate a core for a tooth crown or separate pins. In addition, the template is shaped to accommodate burs used to form holes on the tooth stub which mate with wings on the dental post to prevent the post from rotating after implantation. The dental post of this invention also can be provided with wings extending radially from the leg surfaces which wings mate with indentations on the core surface adjacent to the dental post.

In an alternative version, the dental post has a central hole from the top of the post through to the bottom. A key is passed down the hole from the top and between the legs of the lower section to prevent disengagement of the wings into the root.

Referring to FIGS. 1 through 4, the dental post 10 formed from any suitable dental material includes a top section 12 and a stem section 14. The top section can have a round, oval, square, rectangular or the like cross sections. The top section is straight or angled in relation to the long axis of the post. The area where the post exits the tooth stub is solid which provides maximum strength. The stem section 14 comprises a plurality of legs 16 formed by virtue of a slot 18 which extends through the thickness of the stem section 14. The use of additional slots results in forming additional legs. For convenience, the dental post 10 is shown with two legs. However, it is to be understood that up to eight legs can be formed conveniently with appropriate slots in stem section 14. The wings 20 are secured to or formed integrally with the legs 16 such as by conventional molding, machining or casting processes. The wings 20 are preferably positioned at diametrically opposed positions with respect to each other.

The dental post can be made of a variety of sizes. For example, a dental post can extend about 3 to 18 mm into the root and 1 to 7 mm above the root. A typical dental post diameter can vary between about 0.2 and 2 mm. The wings can extend a length away from the legs a distance between about 0.1 and 2 mm. It is to be understood that these dimensions are exemplary and will vary with the need of the patient. The sides may be parallel or tapered. The top section 12 can be straight or angled to accommodate angled coronal tooth structure.

As shown in FIGS. 2 and 4, the legs can have a semicircular cross-section. As shown in FIG. 3, The wings 17 can have a C-shaped cross-section. The wings 20 can have sharp edges as shown in FIGS. 2 and 3 or the wings 22 can have a curved edge as shown in FIG. 4. The legs 16 are sufficiently flexible so that they can be compressed manually and the bottom edges 24 can be contacted with each other. During this compression step, the wings 20 are moved radially inward toward slot 18. As shown in FIG. 5, a plurality of sets of wings 20, 24 and 26 can be secured to or formed integrally with legs 16.

A set of drill burs which can be utilized in conjunction with the dental post of this invention are shown in FIGS. 6, 7 and 8. Conventional reamers such as gates gliddens and peeso reamers are utilized to form the general gross shape of the tooth bore. The bur 28 includes a shaft 30 to facilitate attachment to a conventional dental drill apparatus and a shaft 32 having smooth ends 34 and 36 and a rough central portion 38. The central portion 38 cuts the tooth to form the bore. The smooth ends 34 and 36 do not cut the tooth so as to minimize or prevent undesirable lateral movement of the bur 28 into the tooth. As shown in FIG. 7, bur 40 includes a shaft 4 having a rough end 42, a smooth central portion 44 and a roughened disk 46. The bur 40 is provided with a shaft 43 for attachment to a conventional dental drill. The end 42 functions to provide a final general shape to the tooth bore while disk 46 provides a smooth surface to the top surface of the tooth stub being treated. The bur 48 of FIG. 8 provides the means for forming the indentations in the walls of the tooth bore into which fit the wings 20 or 22, 24 and/or 26. If it is desired to eliminate indentations for ,sings 24 and 26, disks 49 and 50 having roughened surfaces is of the same general shapes wings 20 and 22. In addition, the top surface of the disc can be smooth to prevent accidental upward movement during use. Also, Bur 48 can be oscillated as represented by arrow 52 to form discrete indentation in the tooth bore wall or can be rotated in contact with the entire bore wall as represented by arrow 53 to form a continuous indentation about the circumference of the bore. It is preferred to form discrete indentations in order to minimize rotation of the post 10 after placement in the tooth bore. An alternative bur to the bur represented in FIG. 8 is shown in FIG. 9. The bur 54 includes a shaft 53 for attachment to a dental drill, a smooth disk 56 and a disk 57 having a roughened surface. As the disk is moved across the top surface of a tooth stub, the surface 57 positioned within a stub forms an indentation.

Referring to FIGS. 10 and 11, a template arrangement 59 is provided comprising a stem formed of a plurality of flexible legs 62 and a slot 60. Legs 62 have small wings 21 that fit into indentations 73 of tooth 71. The legs 62 fit within a tooth bore (see FIG. 16e) so that template 63 rests on the top surface of a tooth stub. A handle 64 is provided so that the template arrangement 59 can be manually inserted into a tooth bore. The template 63 is provided with holes 65 and 66 into which are inserted burs of appropriate size in order to from holes through the top surface of a tooth stub. These holes 65 are provided with parallel surfaces 45 so that straight parallel surfaces can be formed in the holes of the tooth corresponding to template holes 65. These parallel surfaces mate with wings on the dental post to prevent rotation of the post after implantation which will be explained in more detail below. Thereafter one of the cores 67 or 69 of FIGS. 12, 13 or 14 is positioned on the tooth stub by inserting the pins 70 into the holes formed on the top surface of the tooth stub.

Core 67 is provided with slots 85 which mate with wings of a dental post (see FIG. 22) and is provided with internal slots 88 which mate with extension 90 of leg 91 (see FIG. 15). Alternatively, the bore 87 of core 67 can be threaded to mate with threads on the top portion 89. This allows the core to be removed by unscrewing it from the portion 12. Core 69 is provided with internal slots 89 which mate with extension 90. By providing the pins 70 and the internal slots 88 or 89 for the key, the core is secured for maximum retention and maximum resistance to rotation. The core preferably is made of a material which promotes ease of recontour by a dental bur such as a soft composite material. For example, the core can be formed of a metal mesh filled interstitially with a composite material.

Referring to FIGS. 16 a–h, the use of the system of this invention is illustrated. As shown in FIG. 16a, an initial tooth bore 72 is formed with a conventional reamer and filled with a conventional filling material such as a gutta percha based material. In a second step as shown in FIG. 16b, the bur 28 of FIG. 6 is used to shape the bore. The final bore shape is formed with bur 40 of FIG. 7 as shown in FIG. 16c. The bottom surface 93 of the bur 40 is flat thereby forming a flat surface on the remaining filling material 94 in the bottom of the bore. The indentations 73, 74 and 75 in the wall 76 of bore 79 are formed with bur 48 of FIG. 8 as shown in FIG. 16d. The bottom surface 96 of bur 48 contacts the flat surface 97, thereby effecting the proper vertical positioning of burs 49, 50 and 51. The template arrangement 59 of FIGS. 10 and 11 then is inserted into bore 72 and bur 78 is used to form holes 79 through the top surface 80 of tooth stub in FIGS. 16e and f. The template can include wings 22 having a rounded surface. An adhesive is placed within the bore 72 to position the post 10 into the bore 72. Excess adhesive passes upwardly within the bore 72 through slot 18 and exits the tooth stub so the proper amount of adhesive remains within the tooth stub. As shown in FIGS. 16g and h, the post 10 of this invention is inserted into bore 72 followed by positioning of the core 68 on the tooth surface.

Referring to FIG. 17, the drill bur 80 includes a toughened section 82 and smooth sections 83 and 84 to form the wall indentations of a specific shape such as round, triangular or square or the like.

Referring to FIG. 18, a handle 98 having a hollow bore which mates with the top portion 99 of post 10 is provided as a convenient means for inserting the post 10 into the tooth stub and for rotating the post 10 within the tooth stub to position the wings properly therein. After the post has been placed, the handle can be removed by pulling it from the post 10.

Handle 101 of FIG. 19 is formed integrally with one leg at post 10 and has a breakaway point 102 at which the handle can be broken from the post 10 after placement in the tooth bore.

Referring to FIGS. 20 and 21, the template 63 of FIG. 11 can be provided with guide rails 104 which extend above surface 105 and define surfaces 106. Bur 108 having cutting cylinder 110 then can be fit into holes 65 so that bottom surface 112 of bur 108 contacts surfaces 106 and side surface 114 of bur 108 contacts guide rails 104 during use thereby forming holes having parallel surfaces 45.

Referring to FIG. 22, the post 31 includes a plurality of wings 33, a tapered exterior surface 35 and wings on upward legs 31 with wings 37.

Referring to FIG. 23, the post 92 has downward slot 18a forming legs 16a with a plurality of wings 19. An attached template disk 68 has holes 61 which guide placement for pins 77 which pass through holes 61 of template disk 17 into the tooth stub. Pins 77 are parallel or angled to each other or to the long axis of post 10.

Referring to FIG. 24 and 25, the post 122 has downward slot 130 and downward legs 124 with wings 126. Post 122 has central hole 128 which passes from the top to the bottom of post 122. Key 132 passes into central hole 128 and screws downward until it fills slot 130. Key 132 is threaded but can be tapered or straight and threaded or non threaded.

Referring to FIG. 26, post 136 has top section 140 which is angled in relation to the long axis of the stem section 142.

I claim:

1. A dental post for insertion into a bore of a tooth which comprises:
   a top section, a stem attached to said top section having at least one slot extending lengthwise through said stem to form a plurality of spaced apart legs, said legs being substantially parallel to each other and being free of prestress force, at least one of said legs having a wing section extending radially from an outside surface of said legs a distance to fit within an indentation in a wall of said bore in the absence of a force on said legs, each of said legs having a length such that said top section extends beyond a top surface of a tooth when inserted in said tooth, and said legs being movable relative to each other when subjected to a compression force at said free ends such that said wings are removed from an indentation in said wall.

2. The dental post of claim 1 wherein at least one of said legs has a plurality of said wings.

3. The dental post of claim 1 wherein at least one wing on each leg is at essentially the same vertical position as a wing on a second leg.

4. The dental post of claim 1 wherein a surface of said legs is roughened.

5. A dental post for insertion into a bore of a tooth which comprises:
   a top section,
   said top section having at least one slot extending lengthwise through said top section to form a plurality of spaced apart legs, said legs being substantially parallel to each other being free of prestressed force,
   a stem attached to said top section having at least one slot extending lengthwise through said stem to form a plurality of spaced apart legs, said legs being substantially parallel to each other and being free of prestress force,
   at least one of said legs having a wing section extending radially from an outside surface of said legs a distance to fit within an indentation in a wall of said bore in said absence of a force on said legs,
   each of said legs having a length such that said top section extends beyond a top surface of a tooth when inserted in said tooth,
   and said legs being movable relative to each other when subjected to a compression force at said free ends such that said wings are removed from an indentation in said wall.

6. The dental post of claim 5 wherein at least one of said legs on said stem section has a plurality of said wings.

7. The dental post of claim 5 wherein at least one wing on each leg of said stem section is at essentially the same vertical position as a wing on a second leg.

8. The dental post of claim 5 wherein a surface of said legs is roughened.

9. The dental post of claim 5 wherein said legs of said top section of said post includes wings extending from said legs at a position above a top surface of said tooth.

10. The dental post of any one of claims 1, 5, 2, 6, 3, 7, 4, 8 or 9 having two legs.

11. The dental post of any one of claims 1, 5, 2, 6, 3, 7, 4, 8 or 9 and further including a kit comprising:
   a.) a first bur having a cylindrical shaft having a firsts end smooth non-cutting surface, a second end smooth non-cutting surface and an intermediate surface between said first end surface and said second end surface, said intermediate surface comprising a cutting surface.
   b.) a second bur having cylindrical shaft having a first end smooth surface, a first end having a diameter greater than said intermediate smooth surface and having greater than said intermediate smooth surface and having a surface comprising a cutting surface which forms a flat surface on the top of the root stub and a second end comprising a cutting surface to form a flat surface on the bottom surface within a bore of a tooth and
   c.) a third bur comprising a cylindrical smooth main shaft and at least one cylindrical cutting surface secured to said main shaft and having a diameter sufficiently greater than said main shaft so as to form indentations into the wall of said bore wherein a wing and said post fit when said post is inserted into said bore.

12. The dental post of any one of claims 1, 5, 2, 6, 3, 7, 4, 8 or 9 and further including a kit further comprising:
   a.) a first bur having a cylindrical shaft having a first end smooth non-cutting surface, a second end smooth non-cutting surface and an intermediate surface between said first end surface and said second end surface, said intermediate surface comprising a cutting surface.
   b.) a second bur having cylindrical shaft having a first end smooth surface, a first end having a diameter greater than said intermediate smooth surface and having greater than said intermediate smooth surface and having a surface comprising a cutting surface which forms a flat surface on the top of the root stub and a second end comprising a cutting surface to form a flat surface on the bottom surface within a bore of a tooth and
   c.) a third bur comprising a cylindrical smooth main shaft and at least one cylindrical cutting surface secured to said main shaft and having a diameter sufficiently greater than said main shaft so as to form indentations into the wall of said bore wherein a wing and said post fit when said post is inserted into said bore.
   and d.) a template comprising a stem and plate attached to said stem having a size which permits insertion of said stem within a bore of a tooth, said plate having a first set of holes and a second set of holes, said first set of holes permitting communication of a bur with said bore and a top surface of said tooth and said second set of holes permitting communication of a bur with said to surface of said tooth while preventing communication with said bore.

13. The kit of claim 12 wherein said plate of said template includes guide means for a bur to from a hole having parallel surfaces in communication with said bore.

14. The dental post of any one of claims 1, 5, 2, 6, 3, 7, 4, 8 or 9 and further including a kit further comprising:
   a.) a first bur having a cylindrical shaft having a first end smooth non-cutting surface, a second end smooth non-cutting surface and an intermediate surface between said first end surface and said second end surface, said intermediate surface comprising a cutting surface.
   b.) a second bur having cylindrical shaft having a first end smooth surface, a first end having a diameter greater than said intermediate smooth surface and having greater than said intermediate smooth surface and having a surface comprising a cutting surface which forms a flat surface on the top of the root stub and a second end comprising a cutting surface to form a flat surface on the bottom surface within a bore of a tooth and c.) a third bur comprising a cylindrical smooth main shaft and at least one cylindrical cutting surface secured to said main shaft and having a diameter sufficiently greater than said main shaft so as to form indentations into the wall of said bore wherein a wing and said post fit when said post is inserted into said bore.

and d.) a template comprising a stem and plate attached to said stem having a size which permits insertion of said stem within a bore of a tooth, said plate having a first set of holes and a second set of holes, said first set of holes permitting communication of a bur with said bore and a top surface of said tooth and said second set of holes permitting communication of a bur with said to surface of said tooth while preventing communication with said bore.

and f.) a core of a size to be positioned on a top surface of a tooth, said core having a second bore of a size to permit a portion of said post extending above said tooth to be positioned within said second bore, said core having at least one leg of a size to be positioned with holes formed by a bur in said second set of holes in said template.

15. The kit of claim 14 wherein said plate of said template includes guide means for a bur to from a hole having parallel surfaces in communication with said bore.

16. The dental post of any one of claims 1, 5, 2, 6, 3, 7, 4, 8 or 9 and further including a kit further comprising:

a.) a first bur having a cylindrical shaft having a first end smooth non-cutting surface, a second end smooth non-cutting surface and an intermediate surface between said first end surface and said second end surface, said intermediate surface comprising a cutting surface.

b.) a second bur having cylindrical shaft having a first end smooth surface, a first end having a diameter greater than said intermediate smooth surface and having greater than said intermediate smooth surface and having a surface comprising a cutting surface which forms a fiat surface on the top of the root stub and a second end comprising a cutting surface to form a flat surface on the bottom surface within a bore of a tooth and c.) a third bur comprising a cylindrical smooth main shaft and at least one cylindrical cutting surface secured to said main shaft and having a diameter sufficiently greater than said main shaft so as to form indentations into the wall of said bore wherein a wing and said post fit when said post is inserted into said bore.

and d.) a template comprising a stem and plate attached to said stem having a size which permits insertion of said stem within a bore of a tooth, said plate having a first set of holes and a second set of holes, said first set of holes permitting communication of a bur with said bore and a top surface of said tooth and said second set of holes permitting communication of a bur with said to surface of said tooth while preventing communication with said bore.

and e.) a core of a size to be positioned on a top surface of a tooth, said core having a second bore of a size to permit a portion of said post extending above said tooth to be positioned within said second bore, said core having at least one leg of a size to be positioned with holes formed by a bur in said second set of holes in said template.

and f.) a key structure of a size and shape to fit with said slot of said post in a portion of said post extending above said tooth.

17. The kit of claim 16 wherein said plate of said template includes guide means for a bur to from a hole having parallel surfaces in communication with said bore.

18. The kit of claim 16 wherein said core includes second slots within said second bore and a portion of said key fits within said slots.

19. The dental post of any one of claims 1, 5, 2, 6, 3, 7, 4, 8 or 9 further comprising a template attached to said top section between said free end and said wings of said stem section.

20. The dental post of any one of claims 1, 5, 2, 6, 3, 7, 4, 8 or 9 further comprising two legs and a template attached to said top section between said free end and said wings of said stem section.

21. The dental post of any one of claims 1, 5, 2, 6, 3, 7, 4, 8 or 9 further comprising a template attached to said top section between said free end and said wings of said stem section, said template having at least one hole there through and a pin extending through each of said holes.

22. The dental post of any one of claims 1, 5, 2, 6, 3, 7, 4, 8 or 9 further comprising a template attached to said top section between said free end and said wings of said stem section, said template having at least one hole there through and a pin extending through each of said holes, and having two legs.

23. The dental post of any one of claims 1, 5, 2, 6, 3, 7, 4, 8 or 9 further comprising a key extending through said top section and into a space between said legs.

* * * * *